United States Patent
Wucherer et al.

(10) Patent No.: US 10,984,679 B2
(45) Date of Patent: Apr. 20, 2021

(54) MEDICAL SIMULATION SYSTEM, METHOD AND USE

(71) Applicant: Medability GmbH, Munich (DE)

(72) Inventors: Patrick Wucherer, Munich (DE); Stefan Philipp, Munich (DE)

(73) Assignee: MEDABILITY GMBH, Munich (DE)

( * ) Notice: Subject to any disclaimer, the term of this patent is extended or adjusted under 35 U.S.C. 154(b) by 425 days.

(21) Appl. No.: 15/883,998

(22) Filed: Jan. 30, 2018

(65) Prior Publication Data
US 2018/0218649 A1  Aug. 2, 2018

(30) Foreign Application Priority Data
Jan. 31, 2017  (EP) .................................... 17154082

(51) Int. Cl.
| | |
|---|---|
| *G09B 23/32* | (2006.01) |
| *G09B 9/00* | (2006.01) |
| *G09B 23/28* | (2006.01) |
| *G16H 50/50* | (2018.01) |

(52) U.S. Cl.
CPC .............. *G09B 23/32* (2013.01); *G09B 9/00* (2013.01); *G09B 23/285* (2013.01); *G09B 23/286* (2013.01); *G16H 50/50* (2018.01)

(58) Field of Classification Search
CPC .... G09B 23/285; G09B 23/286; G09B 23/32; G09B 9/00
See application file for complete search history.

(56) References Cited

U.S. PATENT DOCUMENTS

| | | | |
|---|---|---|---|
| 6,048,099 A | 4/2000 | Muffett et al. | 383/20 |
| 9,275,556 B1* | 3/2016 | East | G09B 23/285 |
| 9,424,761 B2 | 8/2016 | Tuchschmid et al. | 434/262 |
| 9,607,528 B2* | 3/2017 | Meglan | G09B 23/28 |
| 2013/0189663 A1 | 7/2013 | Tuchschmid et al. | 434/262 |
| 2013/0323700 A1* | 12/2013 | Samosky | G09B 23/28 434/262 |
| 2014/0134586 A1* | 5/2014 | Stein | G09B 23/28 434/262 |

(Continued)

FOREIGN PATENT DOCUMENTS

| | | |
|---|---|---|
| DE | 10 2013 004 843 A | 9/2013 |
| EP | 1 609 431 A1 | 6/2005 |

(Continued)

OTHER PUBLICATIONS

David Fürst, PhD et al., "Transpedicular Approach on a Novel Spine Simulator: A Validation Study", 2018, pp. 1-8, Journal of Surgical Education.

(Continued)

*Primary Examiner* — Eddy Saint-Vil
(74) *Attorney, Agent, or Firm* — Stein IP, LLC

(57) ABSTRACT

The present invention relates to a medical simulation system comprising a physical tissue model; an instrument; and a tracking system adapted to track at least a position and/or an orientation of the physical tissue model and a position and/or an orientation of the instrument, wherein the physical tissue model comprises a tissue model portion and a support structure supporting the tissue model portion and wherein the support structure is elastic. The present invention also relates to a corresponding use and method.

12 Claims, 6 Drawing Sheets

(56) References Cited

U.S. PATENT DOCUMENTS

2015/0230885 A1* 8/2015 Wucher .................. A61C 7/008
 433/24

FOREIGN PATENT DOCUMENTS

EP  3 139 362 A1  3/2017
WO  WO 2009/132067 A1  10/2009

OTHER PUBLICATIONS

E. Moult et al., "Ultrasound-guided facet joint injection training using Perk Tutor", Jan. 18, 2013.
European Examination Report dated Oct. 4, 2020, issued to European Application No. 17 154 082.6.
Pfandler et al.: The Spine J. 17, 1352-1363, Sep. 26, 2013.
Weigl et al.: Surg. Endosc. 30, 559-566, 2015.
Wucherer et al.: IEEE Trans. Med. Imag. 34, 1730-1737, 2015.
Wucherer et al.: Int. J. Comp. Ass. Rad. Surg. 9, 785-794, 2014.
Wucherer et al.: Inf. Proc. Comp.-Assis. Interv. 7915, 1-10, 2013.

* cited by examiner

MEDICAL SIMULATION SYSTEM, METHOD AND USE

INCORPORATION BE REFERENCE

This application is based upon and claims the benefit of priority from the corresponding European Patent Application No. 17154082.6 filed on Jan. 31, 2017, the entire contents of which are incorporated herein by reference.

The present invention relates to a medical simulation system, to a medical simulation method, and to a corresponding use.

Before performing medical interventions, doctors and other healthcare practitioners need to be trained. Classically, such training is performed with cadavers, either of humans or of animals.

However, such classical training has a plurality of shortcomings and disadvantages. For example, depending on the intervention to be performed, such cadavers can only be used once. That is, with such cadavers, it may be hard to repeatedly train a medical intervention. Furthermore, cadavers may be difficult and cumbersome to store and transport. For example, they usually have to be cooled not to deteriorate too quickly. Furthermore, even when properly treated, the properties of cadavers may be different from the properties of live humans or animals. Thus, the realism of the training with cadavers will be far from optimal. Further still, cadavers may be infected with diseases, thereby causing risk to the user.

In light of the above, alternative training systems and methods for medical interventions have been proposed. For example, Moult et al. (Moult, E., Ungi, T., Welch, M. et al. Int J CARS (2013) 8: 831. doi:10.1007/s11548-012-0811-5; in the following simple referred to as "Moult") disclose a medical simulation system comprising a vertebral column model immersed in a gel, a US probe and a needle. The US probe, a reference sensor and the needle are tracked by a tracking system to thereby track their positions and orientations and to be able to visualize the relative positions of these components.

While the medical simulation system of Moult may be satisfactory in some instances, it has certain drawbacks and limitations. In particular, its realism may be far from optimal. Thus, it may not provide training results that are as good as they could be. Furthermore, having a simulation realism which is not optimal may demotivate the users, thereby further deteriorate the training results.

It is an object of the present invention to overcome or at least alleviate the shortcomings and disadvantages of the prior art. In particular, it is an object of the present invention to provide a medical simulation system, method, and use that are more realistic than the prior art.

These objects are met by the present invention.

According to a first embodiment, the present invention relates to a medical simulation system. The medical simulation system comprises a physical tissue model; an instrument; and a tracking system adapted to track at least a position and/or an orientation of the physical tissue model and a position and/or an orientation of the instrument.

As regards the physical tissue model, it is noted that "physical" means that the tissue model "exists" in real space and is not only a computer model of the tissue.

The instrument may be realized in a variety of ways. For example, in some embodiments, the instrument may be a needle or a scalpel. In other embodiments, e.g., when the medical simulation system is configured to simulate a stent insertion, the instrument may be a catheter and/or a stent. All this should be encompassed by the term medical instrument.

Such a medical simulation system may allow for a very realistic medical simulation. The physical tissue model typically is an artificial physical tissue model. Thus, it may be more readily available and more reproducible than cadavers. Furthermore, there may be a decreased risk of infection and the handling of such a system may be lot easier than if cadavers are used. At the same time, having a physical tissue model, that is, a tissue model existing in real space, may provide a very realistic haptic feedback to the user, who may be a healthcare practitioner to be trained. At the same time, by tracking the physical tissue model and the instrument, the system may be enabled to visualize a medical procedure to thereby also provide visual feedback. Thus, one may also train hand-eye coordination with the system. All this may be attained by the discussed system.

The tracking system may be adapted to track a position and an orientation of the physical tissue model and a position and an orientation of the instrument.

The tracking system may comprise a depth sensor, which depth sensor comprises at least one of a 3D camera, a stereo camera, a TOF camera, a lightfield, and a marker based sensor; an optical tracking system; a mechanical tracking system; and/or an ultrasound tracking system. Such sensors may allow for an apt tracking of the physical tissue model and/or the instrument.

The tracking system may comprise an electromagnetic transmitter for generating a magnetic field and sensors, wherein at least one sensor is attached to the physical tissue model and at least one sensor is attached to the instrument. Having the tracking system realized in such a way may also allow for a particularly stable and fail safe tracking. In particular, such an embodiment may allow for the tracking system being independent of the materials being transparent. If compared to, e.g., optical tracking (where the materials used typically need to be transparent for the light used), this may allow for a greater choice of materials.

Each of the instrument and the physical tissue model comprise at least one section adapted for attachment of a sensor.

The at least one section may be adapted to receive the sensor within the section. This may allow for a particularly stable and fail safe attachment of the sensor to the respective section.

The physical tissue model may comprises a tissue model portion and a support structure supporting the tissue model portion.

The support structure may be elastic. The support structure being elastic may denote that the support structure gives way when being supplied with a force typically used during medical procedures. Consider, for example, the simulation of a kyphoplasty. Here, in one step, a trocar (also called hollow needle) is forced into a vertrebra. In the real medical intervention, the tissue may give way when the trocar is forced into the vertebra. This is also simulated in a very realistic manner when the physical tissue model is adapted to give way, i.e., comprises an elastic support structure. Thus, the realism of the simulation may be improved by the provision of the elastic support structure.

The support structure may be adapted to yield by at least 0.1 mm, preferably at least 0.5 mm, more preferably at least 1 mm, such as at least 3 mm when being supplied with a force of 100 N. Such a response of the support structure may correspond to the realistic response a real tissue would have in a real medical intervention. Thus, the realism may be further enhanced by this measure.

The support structure may be a base. The base may also be referred to as a block of a material. The material may be elastic. This may be one option to realize the elastic support structure in a simple manner.

The support structure may comprise at least one spring element. This may be another option to realize the support structure in a simple, fail safe and reproducible manner.

The medical simulation system may further comprise an actuator configured to alter the support structure.

For example, the actuator may be an electrically driven actuator, i.e., an actuator driven by an electric motor. By means of such an actuator, movement of a patient (e.g., the movement due to breathing) may be simulated to make the simulation even more realistic.

The physical tissue model further may comprise a gel at least partially embedding the tissue model portion. For example, the tissue model portion may be hard or solid and may represent one or more vertebrae. Having the gel (or, in other embodiments: foam) may be used to simulate the softer tissue around such a bone structure. Again, this may provide a very realistic feedback to the user to thereby improve the realism of the medical simulation.

The gel may be a silicone rubber gel or a wax gel. For example, the wax gel may be a wax gel commonly used as a gel for candles.

The gel may comprises a viscosity in the range of 10 to 350.000 mPas, preferably 100 to 250.000 mPas, further preferably 1.000 to 200.000 mPas. This may allow for a very realistic simulation of the soft tissue.
The gel may comprise an elastic modulus in the range of 0.01 kPa and 1000 kPa, preferably in the range of 0.1 kPa and 100 kPa. Again, this may allow for a realistic simulation.

Unless otherwise specified, parameters specified herein relate to the parameter under normal pressure (i.e., 1 atm) and at a temperature of 25° C.

The gel may be translucent or transparent.

The physical tissue model may further comprises a foam at least partially embedding the tissue model portion.

The physical tissue model may comprise an elastic layer.

The elastic layer may be made of rubber.

The elastic layer may be arranged on top of the remainder of the physical tissue model.

Generally, the elastic layer may be used to simulate the skin. Having such an elastic layer, which may feel like a barrier layer, may further increase the haptic realism of the simulation. In some embodiments, this elastic layer may have the color of human skin to further increase the realism of the medical simulation.

The tissue model portion may comprise a plurality of portions that are movable with respect to one another. For example, the tissue model portion may represent vertebrae and each of the vertebrae may be movable with respect to the other vertebrae. This may allow for the realistic haptic simulation of a variety of medical interventions where such tissue portions move with respect to one another. As a mere example, with such a system it may be possible to simulate the erection and/or fixation of a fractured vertebra. Thus, having a plurality of different portions that are movable with respect to one another may allow for the simulation of a variety of medical interventions, thereby rendering the system very versatile.

The support structure may comprise one spring element for each such portion. Thus, every such portion may yield individually when being supplied with a force to further enhance the realism of the medical simulation system.

The tracking system may be configured to track a position and an orientation of each of the plurality of the portions. Thus, the system may not only allow for the haptic feedback, i.e., the haptic simulation of such different portions (e.g., different vertebrae), but may also track the movement of such portions to enable the system to also give visual feedback.

The tracking system may comprise one sensor for each of the portions and each of the portions may comprise a section adapted for attachment of one sensor. Again, this may allow for a particularly apt and stable tracking.

The sections may be adapted to receive the sensor within the section.

The instrument may comprise a plurality of instrument sections that are movable with respect to one another. There may a variety of different instruments having sections that are movable with respect to one another. For example, a scissors has two portions that are movable with respect to one another. Furthermore, as discussed, the system may also be used to simulate kyphoplasty, and in particular, to simulate a balloon kyphoplasty. Here, first, a trocar (or hollow tube) is inserted into a vertebra and then a deflated balloon is inserted through the trocar into the vertrebra. The balloon is then inflated to erect the fractured vertebra. The present embodiment allows for a realistic simulation of such an intervention, as the present embodiment allows for the simulation of such instrument sections that are movable with respect to one another. Other instruments having different movable sections include flexible endoscopes and an instrument comprising a cannula and a section to be inserted through the cannula. That is, the section may be moved with respect to the cannula. In some embodiments, such a section may also be steerable, as is the case with the STAR tumor ablation system by Merit Medical Systems, Inc.

The tracking system may be configured to track a position and an orientation of each of the plurality of the instrument sections. Again, the present technology does not only allow for the use of such instruments that have movable section, but also allows for these sections (and thus, their movement) to be tracked. This may allow subsequent visualization of such movement.

The tracking system may comprise one sensor for each of the instrument sections and each of the instrument sections may comprise a section adapted for attachment of one sensor. The sections may be adapted to receive the sensor within the section.

The tissue model portion may be manufactured by additive manufacturing. This may allow for a rapid and individualized manufacturing process of the tissue model portion.

The medical simulation system may comprise a data processing means. The data processing means can be realized in a variety of ways, for example, as a computer, a laptop, a cell phone, a tablet or any of the like.

A tissue model data set may be stored in the data processing means, the tissue model data set corresponding to the physical tissue model.

The data processing means may be configured to alter the tissue model data set based on the tracked position and/or orientation of the physical tissue model. Thus, depending on the position and/or orientation of the physical tissue model in the "real world", the tissue model data set may be altered.

The tissue model data set may be a CT data set. That is, in one embodiment, a CT scan of a patient is performed and used in the subsequent simulation.

The tissue model portion may be manufactured based on the tissue model data set. That is, the tissue model portion may very closely resemble the tissue model data set. For example, in case the tissue model data set is based on a CT scan and the tissue model portion is based on the tissue model data set, the tissue model portion very closely corresponds to the CT scan. That is, the tissue model portion very closely corresponds to the real tissue of the patient. This may be used to train a medical practitioner for a concrete medical intervention. That is, in case of a critical medical intervention to be performed, the medical practitioner (e.g., the surgeon) who will perform this medical intervention, can train this concrete medical intervention in a very realistic scenario.

The data processing means may be configured to alter the tissue model data set based on the tracked positions and/or orientations of the plurality of portions that are movable with respect to one another. For example, the tissue model data set may represent different vertebrae. As discussed, in some embodiments, the physical tissue model may have different portions that are movable with respect to one another. E.g., the physical tissue model may have different vertebrae that are movable with respect to one another, and the movement (i.e., the position and/or orientation) of them may be tracked. The data processing means may be configured to alter the respective tissue model data set in such a scenario. That is, also in the data processing means, the respective "tissue portions" may be moved. Thus, the movement of such portions may also be represented in the data set.

A representation of the instrument may be stored in the data processing means and the data processing means may be configured to alter the representation of the instrument based on the tracked position and/or orientation of the instrument. It will be understood that here, corresponding considerations apply as above with respect to the tracked physical tissue model.

The data processing means may be configured to alter the representation of the instrument based on the tracked positions and/or orientations of the instrument sections.

The data processing means may be configured to alter the tissue model data set based on the tracked position and/or orientation of the instrument and the physical tissue model. For example, in case the instrument is a drill and the physical tissue model represents a bone, there may be provided a hole in the physical tissue model when the drill is in contact with the physical tissue model. This may also be represented in the tissue model data set.

The medical simulation system may further comprise a display device adapted to display an image based on information on the data processing means. In one example, the display device is a monitor. However, it will be understood that the display device may also be realized as a projector (such as a beamer) or augmented reality goggles/head mounted displays e.g. Microsoft HoloLens.

The display device may be configured to display an image based on the tissue model data set and the representation of the instrument.

The medical simulation system may be adapted to adjust an imaging plane of the image.

The medical simulation system may comprise a control unit (160) for adjusting the imaging plane.

The medical simulation system may comprise an actuation element and the medical simulation system may be configured to update the image when the actuation element is actuated. This may allow for a very realistic simulation, e.g., of a medical intervention performed with a C-arm.

The medical simulation system may not comprise a medical imaging device. That is, there may be no real medical imaging device provided in the system and used by the system. This may render the system very simple and avoid the application of, e.g., any radiation to the user.

The medical simulation system may be configured to simulate a medical imaging technique. That is, instead of using a real medical imaging device, the system may only simulate such a medical imaging technique.

The medical simulation system may not comprise a real medical imaging device adapted to perform the medical imaging technique.

The medical simulation system may comprise a dummy device of the medical imaging technique. For example, a dummy of mockup US probe may be used to increase the realism of the system.

The medical simulation system may be configured to simulate at least one of computed tomography, X-ray, magnetic resonance imaging, ultrasound, optical coherence tomography, single photon emission computed tomography, positron emission tomography.

The medical simulation system may further comprise an implant and the tracking system may be adapted to track at least a position and/or an orientation of the implant.

At least one sensor may be attached to the implant.

An implant data set may be stored in the data processing means, and the implant data set may correspond to the implant.

The data processing means may be configured to alter the implant data set based on the tracked position and/or orientation of the implant.

The medical simulation system may further comprise a force sensor adapted to measure a force applied from the instrument to the physical tissue model. Such a force sensor may be used for measuring a force applied by the practitioner on the physical tissue model, e.g., hammering a working cannula through the pedicle into the vertebral body. The obtained information may be used to determine the performance of a practitioner. That is, by the measurements performed by the force sensor, it may be possible to determine whether the procedure was performed correctly, i.e., with the correct force. This may help to further improve the analysis of the training. An exemplary force sensor that may be used is the force sensor FX1901 by Measurement Specialties.

In a further embodiment, the present invention also relates to a use of the medical simulation system discussed above for simulating a medical intervention. It will be understood that any of the features discussed above may also be implemented in connection with such a use. It will further be understood that the use may comprise advantages as the ones discussed above in conjunction with the system.

A healthcare practitioner may be trained by means of the use. In particular, the healthcare practitioner may be trained to perform a certain intervention.

The system may also be used to demonstrate how a particular device functions.

The simulated medical intervention may comprise simulation of medical imaging, which medical imaging comprises at least one of computed tomography, X-ray, magnetic resonance imaging, ultrasound, optical coherence tomography, single photon emission computed tomography, positron emission tomography.

Furthermore, the present invention also relates to a method of simulating a medical intervention, wherein the method uses the medical simulation system discussed above. The method comprises the instrument contacting the physical tissue model; the tracking system tracking a position and/or an orientation of the instrument; and the tracking system tracking a position and/or an orientation of the physical tissue model. Again, it will be understood that any of the features discussed above in conjunction with the system may also be realized in the method and that the method may have advantages corresponding to the ones discussed above.

The method may comprise: the tracking system tracking a position and an orientation of the instrument; and the tracking system tracking a position and an orientation of the physical tissue model.

The method may comprise: the support structure being compressed due to a force being supplied to the physical tissue model.

The method may comprise: the base being compressed by at least 0.1 mm, preferably at least 0.5 mm, more preferably at least 1 mm, such as at least 3 mm.

The method may comprise: moving the movable portions with respect to one another.

The method may comprise: the tracking system tracking the position and the orientation of the plurality of portions.

The method may comprise: moving the instrument sections with respect to one another; and the tracking system tracking the position and the orientation of the instrument sections.

The method may comprise: the data processing means altering the tissue model data set based on the tracked position and/or orientation of the physical tissue model.

The method may comprise: the data processing means altering the tissue model data set based on the tracked positions and/or orientations of the portions.

The method may comprise: the data processing means altering the representation of the instrument based on the tracked position and/or orientation of the instrument.

The method may comprise: the data processing means altering the tissue model data set based on the tracked position and/or orientation of the instrument and the physical tissue model.

The method may comprise: the display device displaying an image based on information on the data processing means.

The displayed image may be based on the tissue model data set and the representation of the instrument.

The method may comprise: adjusting an imaging plane of the image.

The method may comprise: updating the image when the actuation element is actuated.

The method may comprise: simulating a medical imaging comprising at least one of computed tomography, X-ray, magnetic resonance imaging, ultrasound, optical coherence tomography, single photon emission computed tomography, positron emission tomography.

The method may comprise: the data processing means altering the implant data set based on the tracked position and/or orientation of the implant.

The method may comprise: the actuator altering the support structure.

Thus, a movement of a patient (e.g., breathing) may be simulated.

It will be understood that the above discussed embodiments relate to a system providing a very realistic, stable and fail safe medical simulation.

Furthermore, the present invention also relates to the below discussed numbered embodiments.

Below, system embodiments will be discussed. These embodiments are designated by the letter S followed by a number. When reference is herein made to system embodiments, those embodiments are meant.

S1. A medical simulation system comprising
a physical tissue model;
an instrument; and
a tracking system adapted to track at least a position and/or an orientation of the physical tissue model and a position and/or an orientation of the instrument.

As regards the physical tissue model, it is noted that "physical" means that the tissue model "exists" in real space and is not only a computer model of the tissue.

The instrument may be realized in a variety of ways. For example, in some embodiments, the instrument may be a needle or a scalpel. In other embodiments, e.g., when the medical simulation system is configured to simulate a stent insertion, the instrument may be a catheter and/or a stent. All this should be encompassed by the term medical instrument.

S2. The medical simulation system according to embodiment 1, wherein the tracking system is adapted to track a position and an orientation of the physical tissue model and a position and an orientation of the instrument.

S3. The medical simulation system according to any of the preceding embodiments, wherein the tracking system comprises a depth sensor, which depth sensor comprises at least one of a 3D camera, a stereo camera, a TOF camera, a lightheld, and a marker based sensor; an optical tracking system; a mechanical tracking system; and/or an ultrasound tracking system.

S4. The medical simulation system according to any of the preceding embodiments, wherein the tracking system comprises an electromagnetic transmitter for generating a magnetic field and sensors, wherein at least one sensor is attached to the physical tissue model and at least one sensor is attached to the instrument.

S5. The medical simulation system according to the preceding embodiment, wherein each of the instrument and the physical tissue model comprise at least one section adapted for attachment of a sensor.

S6. The medical simulation system according to the preceding embodiment, wherein the at least one section is adapted to receive the sensor within the section.

S7. The medical simulation system according to any of the preceding embodiments, wherein the physical tissue model comprises a tissue model portion and a support structure supporting the tissue model portion.

S8. The medical simulation system according to the preceding embodiment, wherein the support structure is elastic.

S9. The medical simulation system according to the preceding embodiment, wherein the support structure is adapted to yield by at least 0.1 mm, preferably at least 0.5 mm, more preferably at least 1 mm, such as at least 3 mm when being supplied with a force of 100 N.

S10. The medical simulation system according to any of the 3 preceding embodiments, wherein the support structure is a base.

The base may also be referred to as a block of a material. The material may be elastic.

S11. The medical simulation system according to any of the embodiments S7 to S9, wherein the support structure comprises at least one spring element.

S12. The medical simulation system according to any of the preceding embodiments with the features of embodiment S7, wherein the medical simulation system further comprises an actuator configured to alter the support structure.

For example, the actuator may be an electrically driven actuator, i.e., an actuator driven by an electric motor. By means of such an actuator, movement of a patient (e.g., the movement due to breathing) may be simulated to make the simulation even more realistic.

S13. The medical simulation system according to any of the 5 preceding embodiments, wherein the physical tissue model further comprises a gel at least partially embedding the tissue model portion.

S14. The medical simulation system according to the preceding embodiment, wherein the gel is a silicone rubber gel or a wax gel.

For example, the wax gel may be a wax gel commonly used as a gel for candles.

S15. The medical simulation system according to any of the 3 preceding embodiments, wherein the gel comprises a viscosity in the range of 10 to 350.000 mPas, preferably 100 to 250.000 mPas, further preferably 1.000 to 200.000 mPas.

Unless otherwise specified, parameters specified herein relate to the parameter under normal pressure (i.e., 1 atm) and at a temperature of 25° C.

S15a. The medical simulation system according to any of the 3 preceding embodiments, wherein the gel comprises an elastic modulus in the range of 0.01 kPa and 1000 kPa, preferably in the range of 0.1 kPa and 100 kPa.

S16. The medical simulation system according to any of the 4 preceding embodiments, wherein the gel is translucent or transparent.

S17. The medical simulation system according to any of the embodiments S7 to S11, wherein the physical tissue model further comprises a foam at least partially embedding the tissue model portion.

S18. The medical simulation system according to any of the preceding embodiments, wherein the physical tissue model comprises an elastic layer.

S19. The medical simulation system according to the preceding embodiment, wherein the elastic layer is made of rubber.

S20. The medical simulation system according to any of the 2 preceding embodiments, wherein the elastic layer is arranged on top of the remainder of the physical tissue model.

S21. The medical simulation system according to any of the preceding embodiments with the features of embodiment S7, wherein the tissue model portion comprises a plurality of portions that are movable with respect to one another.

S22. The medical simulation system according to the preceding embodiment and with the features of embodiment S11, wherein the support structure comprises one spring element for each portion.

S23. The medical simulation system according to any of the preceding 2 embodiments, wherein the tracking system is configured to track a position and an orientation of each of the plurality of the portions.

S24. The medical simulation system according to the preceding embodiment and with the features of embodiment S4, wherein the tracking system comprises one sensor for each of the portions and further wherein each of the portions comprises a section adapted for attachment of one sensor.

S25. The medical simulation system according to the preceding embodiment, wherein the sections are adapted to receive the sensor within the section.

S26. The medical simulation system according to any of the preceding embodiments, wherein the instrument comprises a plurality of instrument sections that are movable with respect to one another.

S27. The medical simulation system according to the preceding embodiment, wherein the tracking system is configured to track a position and an orientation of each of the plurality of the instrument sections.

S28. The medical simulation system according to the preceding embodiment and with the features of embodiment S4, wherein the tracking system comprises one sensor for each of the instrument sections and further wherein each of the instrument sections comprises a section adapted for attachment of one sensor.

S29. The medical simulation system according to the preceding embodiment, wherein the sections are adapted to receive the sensor within the section.

S30. The medical simulation system according to any of the preceding embodiments with the feature of embodiment S7, wherein the tissue model portion is manufactured by additive manufacturing.

S31. The medical simulation system according to any of the preceding embodiments, wherein the medical simulation system comprises a data processing means.

S32. The medical simulation system according to the preceding embodiment, wherein a tissue model data set is stored in the data processing means, the tissue model data set corresponding to the physical tissue model.

S33. The medical simulation system according to the preceding embodiment, wherein the data processing means is configured to alter the tissue model data set based on the tracked position and/or orientation of the physical tissue model.

S34. The medical simulation system according to any of the 2 preceding embodiments, wherein the tissue model data set is a CT data set.

S35. The medical simulation system according to any of the 3 preceding embodiments and with the features of embodiment S30, wherein the tissue model portion is manufactured based on the tissue model data set.

S36. The medical simulation system according to any of the 4 preceding embodiments and with the features of embodiment S23, wherein the data processing means is configured to alter the tissue model data set based on the tracked positions and/or orientations of the plurality of portions that are movable with respect to one another.

S37. The medical simulation system according to any of the 6 preceding embodiments, wherein a representation of the instrument is stored in the data processing means and wherein the data processing means is configured to alter the representation of the instrument based on the tracked position and/or orientation of the instrument.

S38. The medical simulation system according to the preceding embodiment and with the features of embodiment S27, wherein the data processing means is configured to alter the representation of the instrument based on the tracked positions and/or orientations of the instrument sections.

S39. The medical simulation system according to any of the preceding embodiments with the features of embodiment S32, wherein the data processing means is configured to alter the tissue model data set based on the tracked position and/or orientation of the instrument and the physical tissue model.

For example, in case the instrument is a drill and the physical tissue model represents a bone, there may be provided a hole in the physical tissue model when the drill is in contact with the physical tissue model. This may also be represented in the tissue model data set.

S40. The medical simulation system according to any of the preceding embodiments with the features of embodiment S31, wherein the medical simulation system further comprises a display device adapted to display an image based on information on the data processing means.

S41. The medical simulation system according to the preceding embodiment and with the features of embodiments S32 and S37, wherein the display device is configured to display an image based on the tissue model data set and the representation of the instrument.

S42. The medical simulation system according to any of the preceding 2 embodiments, wherein the medical simulation system is adapted to adjust an imaging plane of the image.

S43. The medical simulation system according to the preceding embodiment, wherein the medical simulation system comprises a control unit for adjusting the imaging plane.

S44. The medical simulation system according to any of the preceding embodiments with the features of embodiment S40, wherein the medical simulation system comprises an actuation element and wherein the medical simulation system is configured to update the image when the actuation element is actuated.

S45. The medical simulation system according to any of the preceding embodiments, wherein the medical simulation system does not comprise a medical imaging device.

S46. The medical simulation system according to any of the preceding embodiments, wherein the medical simulation system is configured to simulate a medical imaging technique.

S47. The medical simulation system according to the preceding embodiment, wherein the medical simulation system does not comprise a real medical imaging device adapted to perform the medical imaging technique.

S48. The medical simulation system according to any of the 2 preceding embodiments, wherein the medical simulation system comprises a dummy device of the medical imaging technique.

S49. The medical simulation system according to any of the 3 the preceding embodiments, wherein the medical simulation system is configured to simulate at least one of computed tomography, X-ray, magnetic resonance imaging, ultrasound, optical coherence tomography, single photon emission computed tomography, positron emission tomography.

S50. The medical simulation system according to any of the preceding embodiments, wherein the medical simulation system further comprises an implant and wherein the tracking system is adapted to track at least a position and/or an orientation of the implant.

S51. The medical simulation system according to the preceding embodiment and with the features of embodiment S31, wherein at least one sensor is attached to the implant.

S52. The medical simulation system according to the preceding embodiment and with the features of embodiment S27, wherein an implant data set is stored in the data processing means, the implant data set corresponding to the implant.

S53. The medical simulation system according to the preceding embodiment, wherein the data processing means is configured to alter the implant data set based on the tracked position and/or orientation of the implant.

S54. The medical simulation system according to any of the preceding embodiments, wherein the medical simulation system further comprises a force sensor adapted to measure a force applied from the instrument to the physical tissue model.

Below, use embodiments will be discussed. These embodiments are designated by the letter U followed by a number. When reference is herein made to use embodiments, those embodiments are meant.

U1. Use of the medical simulation system according to any of the preceding embodiments for simulating a medical intervention.

U2. Use according to the preceding embodiment, wherein a healthcare practitioner is trained.

U3. Use according to any of the 2 preceding embodiments, wherein the simulated medical intervention comprises simulation of medical imaging, which medical imaging comprises at least one of computed tomography, X-ray, magnetic resonance imaging, ultrasound, optical coherence tomography, single photon emission computed tomography, positron emission tomography.

Below, method embodiments will be discussed. These embodiments are designated by the letter M followed by a number. When reference is herein made to method embodiments, those embodiments are meant.

M1. A method of simulating a medical intervention, wherein the method uses the medical simulation system according to any of the preceding system embodiments, the method comprising
the instrument contacting the physical tissue model;
the tracking system tracking a position and/or an orientation of the instrument; and
the tracking system tracking a position and/or an orientation of the physical tissue model.

M2. The method according to the preceding embodiment, wherein the method further comprises
the tracking system tracking a position and an orientation of the instrument; and
the tracking system tracking a position and an orientation of the physical tissue model.

M3. The method according to any of the preceding method embodiments, wherein the medical simulation system comprises the features of embodiment S9, wherein the method further comprises
the support structure being compressed due to a force being supplied to the physical tissue model.

M4. The method according to the preceding embodiment, wherein the base is compressed by at least 0.1 mm, preferably at least 0.5 mm, more preferably at least 1 mm, such as at least 3 mm.

M5. The method according to any of the preceding method embodiments, wherein the medical simulation system comprises the features of embodiment S21, wherein the method further comprises
moving the portions with respect to one another.

M6. The method according to any of the preceding method embodiments, wherein the medical simulation system comprises the features of embodiment S23, wherein the method further comprises
the tracking system tracking the position and the orientation of the plurality of portions.

M7. The method according to any of the preceding method embodiments, wherein the medical simulation system comprises the features of embodiment S27, wherein the method further comprises
moving the instrument sections with respect to one another; and
the tracking system tracking the position and the orientation of the instrument sections.

M8. The method according to any of the preceding method embodiments, wherein the medical simulation system comprises the features of embodiment S33, wherein the method further comprises
the data processing means altering the tissue model data set based on the tracked position and/or orientation of the physical tissue model.

M9. The method according to any of the preceding method embodiments, wherein the medical simulation system comprises the features of embodiment S33, wherein the method further comprises the data processing means altering the tissue model data set based on the tracked positions and/or orientations of the portions.

M10. The method according to any of the preceding method embodiments, wherein the medical simulation system comprises the features of embodiment S37, wherein the method further comprises the data processing means altering the representation of the instrument based on the tracked position and/or orientation of the instrument.

M11. The method according to any of the preceding method embodiments, wherein the medical simulation system comprises the features of embodiment S39, wherein the method further comprises the data processing means altering the tissue model data set based on the tracked position and/or orientation of the instrument and the physical tissue model.

M12. The method according to any of the preceding method embodiments, wherein the medical simulation system comprises the features of embodiment S40, wherein the method further comprises the display device displaying an image based on information on the data processing means.

M13. The method according to any of the preceding method embodiments, wherein the medical simulation system comprises the features of embodiment S41, wherein the displayed image is based on the tissue model data set and the representation of the instrument.

M14. The method according to any of the preceding method embodiments, wherein the medical simulation system comprises the features of embodiment S42, wherein the method further comprises adjusting an imaging plane of the image.

M15. The method according to any of the preceding method embodiments, wherein the medical simulation system comprises the features of embodiment S44, wherein the method further comprises updating the image when the actuation element is actuated.

M16. The method according to any of the preceding method embodiments, wherein the method comprises simulating a medical imaging comprising at least one of computed tomography, X-ray, magnetic resonance imaging, ultrasound, optical coherence tomography, single photon emission computed tomography, positron emission tomography.

M17. The method according to any of the preceding method embodiments, wherein the medical simulation system comprises the features of embodiment S53, wherein the method further comprises the data processing means altering the implant data set based on the tracked position and/or orientation of the implant.

M18. The method according to any of the preceding method embodiments, wherein the medical simulation system comprises the features of embodiment S12, wherein the method further comprises the actuator altering the support structure.

Thus, a movement of a patient (e.g., breathing) may be simulated.

The present invention will now be described with reference to the accompanying drawings and exemplary embodiments. The discussed embodiments are intended to exemplify, but not to limit, the scope of the present invention.

Figure 1:
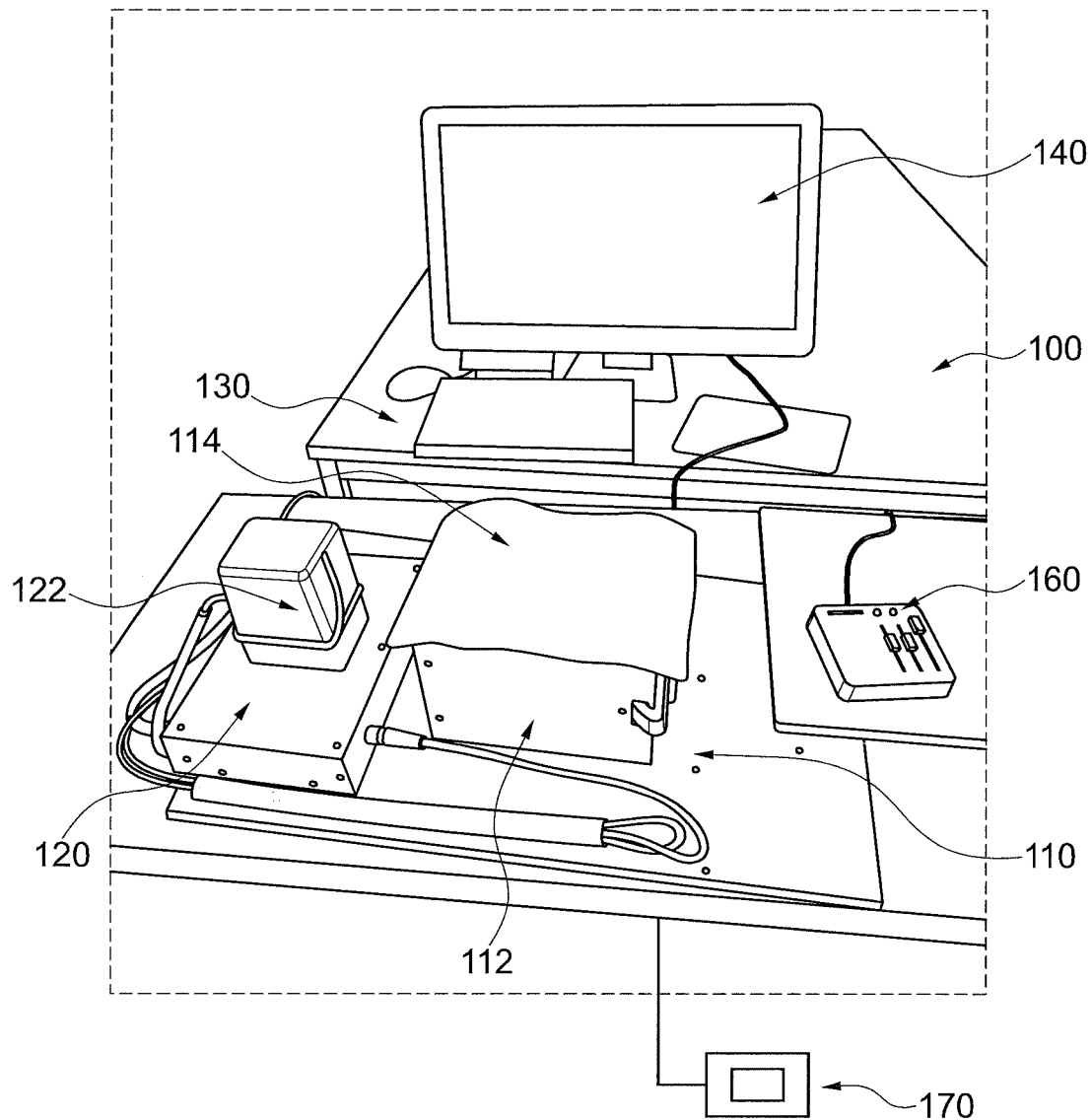
FIG. 1 depicts a medical simulation system in accordance with an embodiment of the present invention.

FIG. 1 depicts an exemplary medical simulation system 100 for simulating at least one medical intervention. The medical simulation ("MS") system 100 comprises a physical tissue model 110, a tracking system 120, a data processing means 130, which is here realized as a laptop computer and a display device 140, which is here realized as a computer monitor. Though not depicted in FIG. 1, but in FIG. 2, the MS system 100 also comprises an instrument 150, such as a needle.

Figure 3:
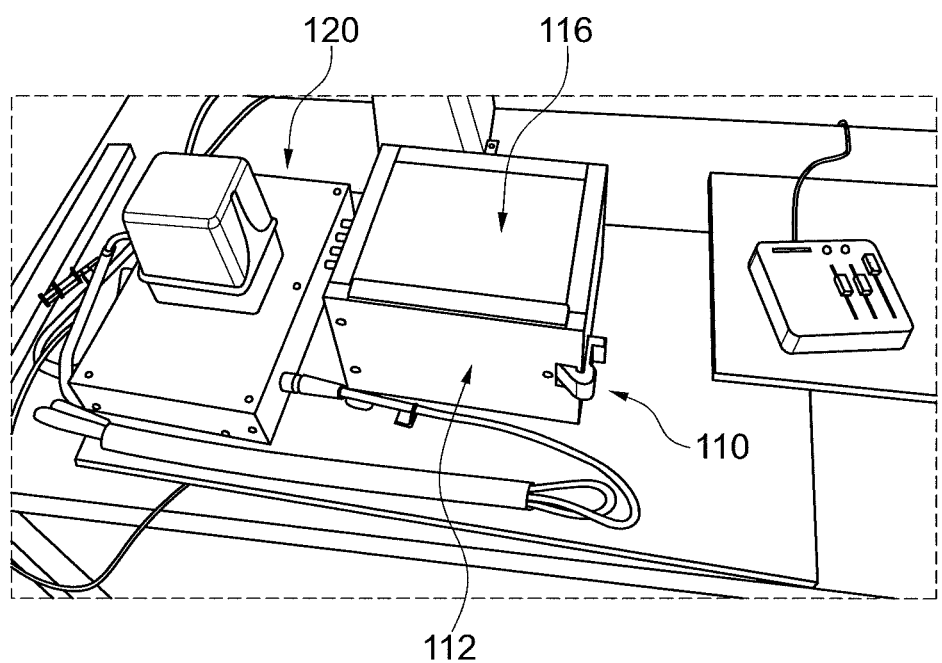
FIG. 3 depicts a portion of the system of FIG. 1.
Figure 4:
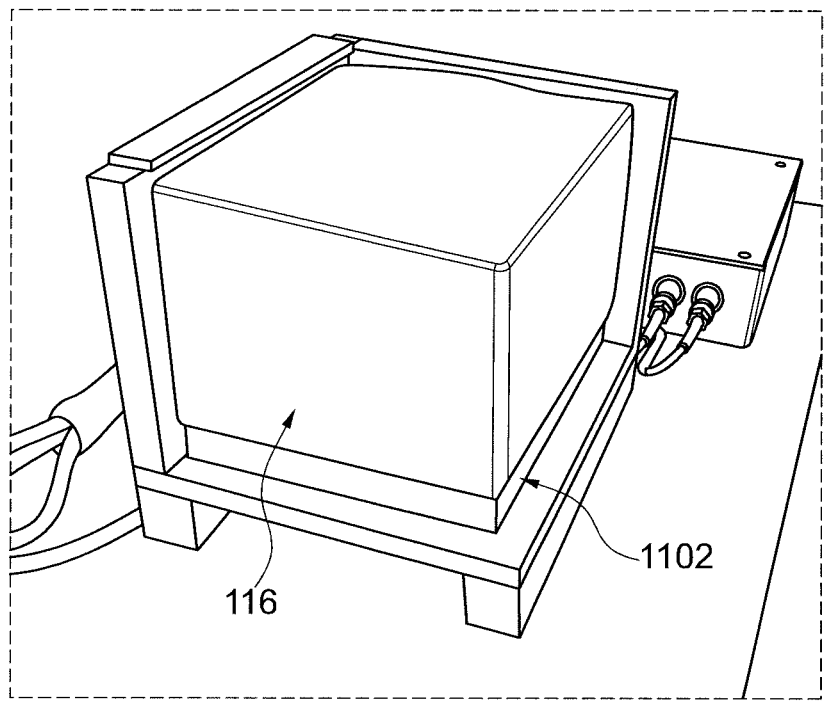
FIG. 4 depicts a physical tissue model to be employed in embodiments of the present invention.

The physical tissue model 110 generally comprises a housing 112 that may be open to one side and particularly to the top side. When terms like "top" and "bottom" are used herein, these terms denote the position in the normal use configuration of the MS system 100, unless specified otherwise or unless clear to the skilled person that something different is meant. The open top side of the housing 112 is covered by an elastic layer 114, which elastic layer 114 may be made of rubber, for example. The elastic layer 114 has been removed in FIG. 3 to expose the portions of the physical tissue model 110 inside the housing 112. As is visible in FIG. 3, the housing 112 houses a portion of gel 116 (however, in other embodiments, foam may also be used instead of the gel). This is also visible in FIG. 4, where two side portions of the housing 112 have also been removed to thereby expose a block of gel 116.

Figure 5:
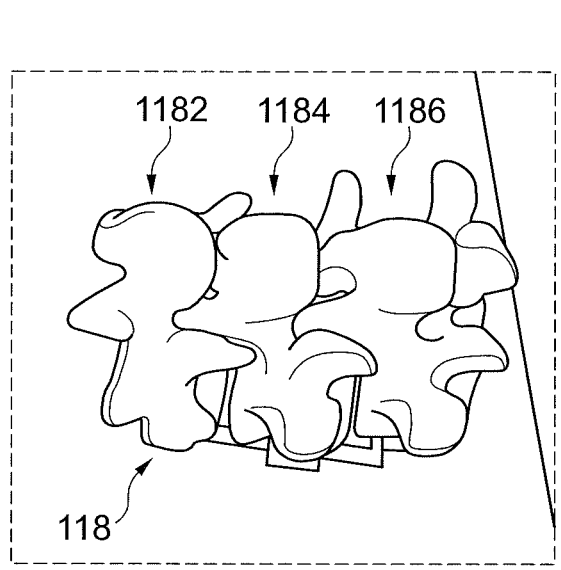
FIG. 5 depicts an exemplary tissue model portion to be employed in embodiments of the present invention.
Figure 6:
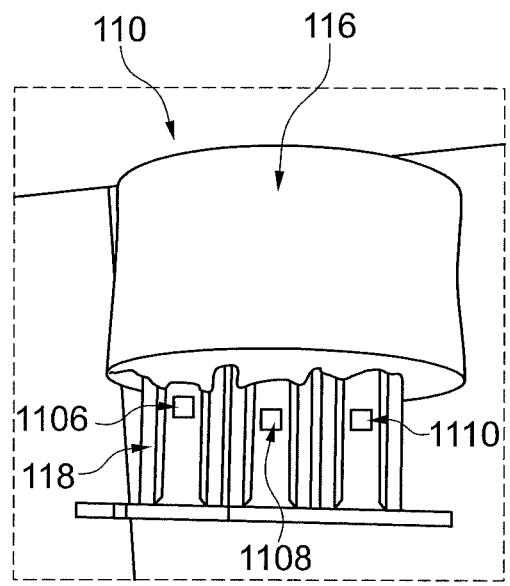
FIG. 6 depicts a further variant of a tissue model portion embedded in a gel to be employed in embodiments of the present invention.
Figure 7:
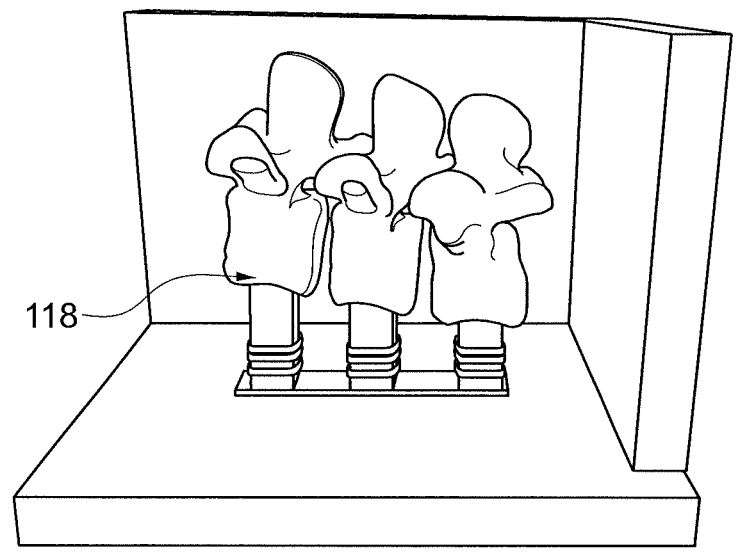
FIG. 7 depicts a still further variant of a tissue model portion to be employed in embodiments of the present invention.
Figure 8:
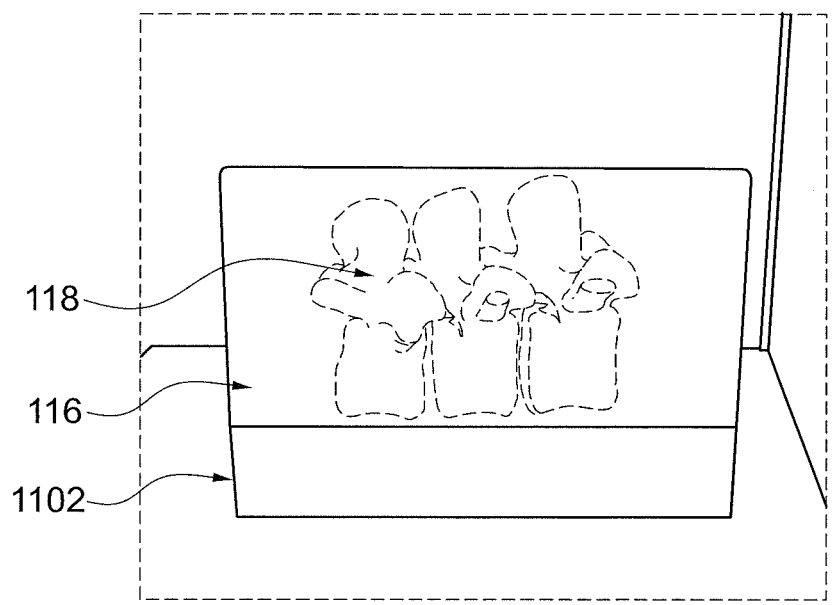
FIG. 8 depicts a still further variant of a tissue model portion embedded in a gel and supported on a base, to be employed in embodiments of the present invention.

Embedded in the gel 116 is a solid bone model 118 that may be made of solid plastic material, as is depicted in FIG. 5. FIG. 6 depicts a further variant of a portion of gel 116, which at least partially embeds a solid bone model 118. A further variant of the solid bone model 118, which may generally also be referred to as a tissue model portion 118, is also depicted in FIG. 7. FIG. 8 depicts another version of a tissue model portion 118 (such as a solid bone model)

embedded in a gel 116 and supported by a support structure, which is here realized as a base 1102, which base 1102 may be resilient or elastic.

Generally speaking, the physical tissue model 110 may comprise the housing 112 and the tissue model portion 118 located in the housing 112. Furthermore, the physical tissue model 110 also comprises a portion of gel 116 located in the housing 112 and at least partially enclosing or embedding the tissue model portion 118, which is here realized as a solid bone model 118. The physical tissue model 110 may also comprise the elastic layer 114 constituting a skin model in the physical tissue model 110.

It will be understood that the physical tissue model 110 may be used in conjunction with the instrument 150 to simulate a medical intervention and to provide a haptic feedback in such a medical intervention simulation. That is, turning to FIG. 1, the instrument 150 may be pushed through the elastic layer 114 of the physical tissue model 110 and may then be pushed through the gel 116 (representing the soft tissue) until the instrument 150 reaches the solid bone model 118 and then may be advanced into the solid bone model 118. Here, a medical intervention may be performed. Exemplary medical interventions to be performed may include vertebroplasty, kyphoplasty, tumor ablation, sacroiliac joint injection/fusion, facet joint injection, spondylodesis (spinal fusion), vertebral body replacement, pedicle screw fixation, endoscopy, biopsy, pain therapy, nerve ablation, and/or implant insertion.

While the above may be sufficient to provide haptic feedback to the user, i.e., to the person performing the training, it may also be desirable to provide visual feedback and to provide a simulation of the imaging. This may be achieved as follows.

The physical tissue model 110 typically has a corresponding or matching data tissue model, which may also be referred to as a tissue model data set. For example, the physical tissue model 110 may be generated by means of a matching data tissue model.

One example is that the data tissue model is first generated by means of an imaging process of a real person/a real patient. That is, an imaging process (e.g., a CT scan, CBCT, MRI, US or a combination thereof) is performed on a real body, thus resulting in a 3D data set of the tissue of the body. The 3D data set is the data tissue model, e.g., of a section of the vertebral column. Based on this 3D data set (i.e., the data tissue model), the physical tissue model 110 may be generated, e.g., by means of additive manufacturing, such as 3D printing.

Thus, there is a data tissue model (also referred to as 3D tissue data set) corresponding to the physical tissue model. It will be understood that to also provide visual feedback to the user, an image based on the data tissue model may be displayed by means of the display device 140.

Figure 12:
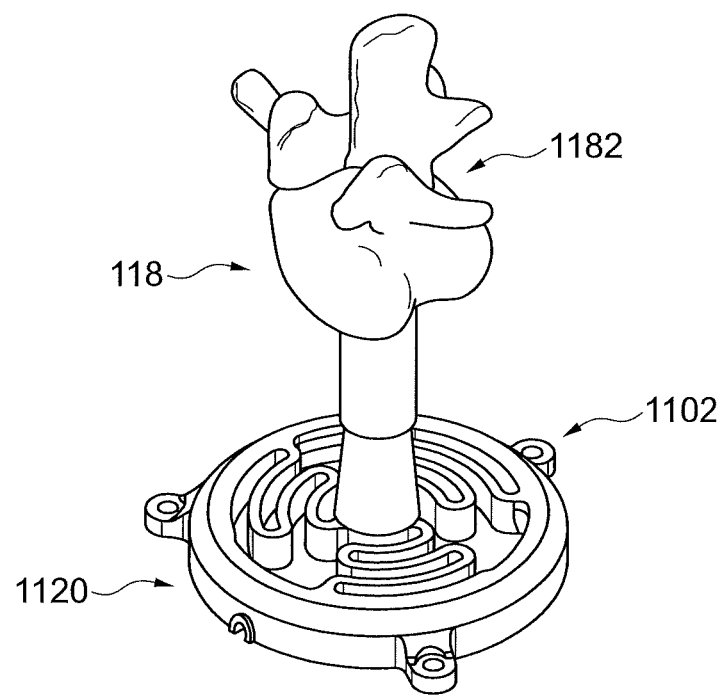
FIG. 12 depicts a variant of parts of a physical tissue model in accordance with an embodiment of the present invention.

It may be of particular interest that the physical tissue model 110 is movable, i.e., that it can change its position. This may improve the realism of the MS system 100 and the corresponding method. For example, it will be understood that when a medical practitioner would use the needle 150 in a real medical intervention and would force it into a body, the body would yield or give way slightly due to the force applied by means of the needle 150, in particular when the needle reaches a bone and a force is supplied. That is, in such a scenario, the body would be forced down by means of the pressure supplied to the needle 150. This may also be simulated by the present embodiment of the MS system 100. In particular, the physical tissue model 110 may comprise a support structure, which may be an elastic base 1102 supporting the solid bone model 118 and the gel 116 (though foam may also be used instead of the gel). When a pressure/force is supplied to the physical tissue model 110 (e.g., when the instrument 150 contacts the solid bone model 118 and a pressure is supplied to this solid bone model 118), the elastic base 1102 may yield under this pressure and give way. Thus, the solid bone model 118 may move in response to such a pressure/force. This may lead to a particularly realistic behavior and haptic feedback of the MS system 100. For example, the elastic base 1102 may be formed of silicone. In the above discussed embodiments, the support structure was realized as an elastic base 1102. However, the support structure may also be realized in different manners. For example, FIG. 12 depicts a further embodiment of parts of a physical tissue model. Again, the physical tissue model comprises a solid bone model 118 having a vertebra model 1182. The solid bone model 118 in this embodiment is also supported on a support structure 1102, which comprises a spring construction 1120. Again, by means of such an elastic support structure 1102, the physical tissue model 110 may yield when being supplied with a force, which may provide a more realistic feedback to a user. As a mere example, one may supply a force of approximately 100 N (roughly corresponding to 10 kg of weight) to the physical tissue model 110 and more particularly to the vertebra 1182. That is, one may press the vertebra 1182 down with a force of 100 N. More particularly, one may press the vertebra 1182 down with an instrument having a surface of 0.2 cm×0.2 cm contacting the vertebra 1182. In such a scenario, the elastic support structure 1102, may yield by at least 0.1 mm when supplied with a force of 100 N, more preferably by at least 1 mm, such as at least 3 mm and up to 5 cm. This may provide the user with a realistic feedback. Thus, when the physical tissue model is supplied with the forces that may occur in real medical interventions (such as during hammering, pushing, expanding exerted by medical instruments), the physical tissue model may yield in a realistic manner.

Figure 13:
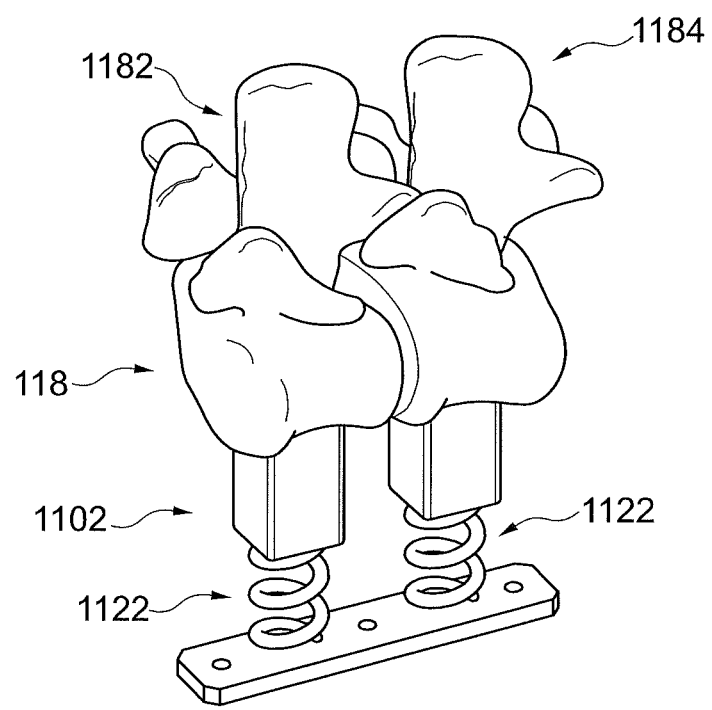
FIG. 13 depicts a still further variant of parts of a physical tissue model in accordance with another embodiment of the present invention.

FIG. 13 depicts a further variant of parts of a physical tissue model in accordance with a still further embodiment. The physical tissue model of FIG. 13 again comprises a solid bone model 118 comprising vertebra portions 1182, 1184. The physical tissue model also comprises an elastic support structure 1102, which comprises springs 1122, and more particularly one spring 1122 for each vertebra portion 1182, 1184. It will be understood that the embodiment in FIG. 13 also allows for the vertebra portions 1182 to yield when supplied with a force. Furthermore, the embodiment in FIG. 13 also allows for the different vertebra portions 1182, 1184 (or, more generally, for the different tissue portions) to move relative to one another.

As discussed, FIGS. 12 and 13 depict parts of a physical tissue model. It will be understood that when used, e.g., in the system 100 depicted in FIG. 1, further elements will typically be added to the parts of the physical tissue model depicted in FIGS. 12 and 13. For example, e.g., the gel 116 (or a foam) is typically used in conjunction with the parts depicted in FIGS. 12 and 13. Furthermore (though not depicted), the embodiments in FIGS. 12 and 13 also typically comprise sensor attachment sections 1106 as discussed, e.g., in conjunction with FIG. 6.

It may generally also be desirable that a movement of the physical tissue model 110 is also made visible by the display device 140. As discussed, the display device 140 may display a picture (also referred to as an image) corresponding to the data tissue model, which data tissue model matches the physical tissue model 110. However, to be able to visualize such a movement, the MS system 100 has to sense the movement (i.e., the change of location) of the physical tissue model 110. This may be done by means of the tracking system 120.

Figure 11:
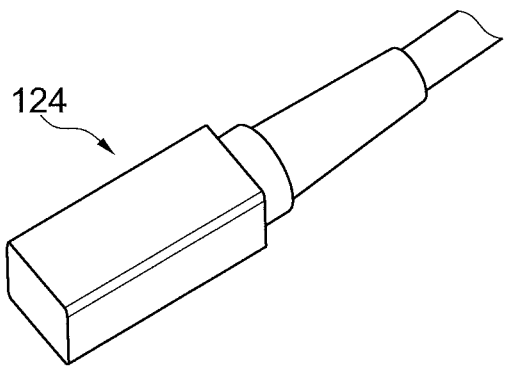
FIG. 11 depicts a sensor to be employed in embodiments of the present invention.

Generally, the tracking system 120 may sense or track the position and/or the orientation of other devices. In the depicted embodiment, the tracking system 120 is realized as an electromagnetic tracking system 120. For example, the trakSTAR or driveBAY systems of Ascension Technology Corporation can be used as an electromagnetic tracking system 120. The electromagnetic tracking system 120 comprises an electromagnetic transmitter 122 establishing a magnetic field. Furthermore, the tracking system 120 also comprises sensors 124, an example of which is depicted in FIG. 11. The sensors 124 may also be referred to as beads 124. The sensors 124 are adapted to sense the generated magnetic field. Thus, by means of the field measured by a sensor 124, the location and the position of the sensor 124 can be determined. It will be understood that this allow the tracking system 120 to determine the position and orientation of the sensor 124.

Figure 9:
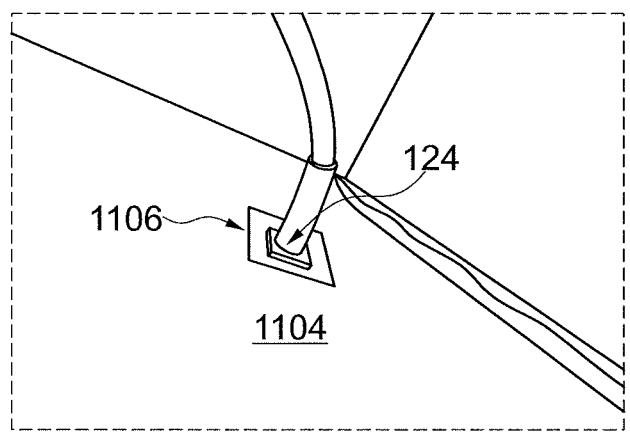
FIG. 9 depicts a section of a physical tissue model and a sensor to be employed in embodiments of the present invention.

The sensor 124 (or, in some embodiments: the sensors 124) may be attached to the physical tissue model 110 in a defined manner. Thus, by means of sensing the position and orientation of the sensor 124, one may sense the position and orientation of the physical tissue model 110. In that regard, reference is first made to FIG. 9 depicting a section 1104 of the physical tissue model 110, and more particularly a bottom side or bottom surface 1104 thereof. When an embodiment with a resilient base 1102 is used, the bottom surface 1104 typically is the bottom surface of the resilient base 1102. As can be seen, the physical tissue model 110 comprises a section 1106 adapted for attachment of the sensor 124. In the depicted embodiment, the section 1106 is a recess adapted to receive the sensor 124. It will be understood that when the sensor 124 is attached to the physical tissue model 110 (e.g., received in a recess 1106 of the physical tissue model 110) in a defined manner, also the position and orientation of the physical tissue model 110 can be determined.

In the above, it has been described how the position and/or orientation of the physical tissue model 110 can be determined by means of the tracking system 120. As also discussed, the position of the physical tissue model 110 can be changed, e.g., due to force being supplied thereto, for example when the instrument 150 is used and pressed against the solid bone model 118. Such a change of the position will then be sensed or tracked by the tracking system 120. Furthermore, such a change may also be displayed by the display device 140. That is, when the MS system 100 senses a change of the position and/or orientation of the physical tissue model 110, the position and/or orientation of the data tissue model may be changed accordingly and this may be displayed. Thus, not only the physical tissue model 110 may be movable (and the movements trackable), but the movements may also be displayed by the display device 140 to provide an even more realistic medical simulation.

Figure 2:
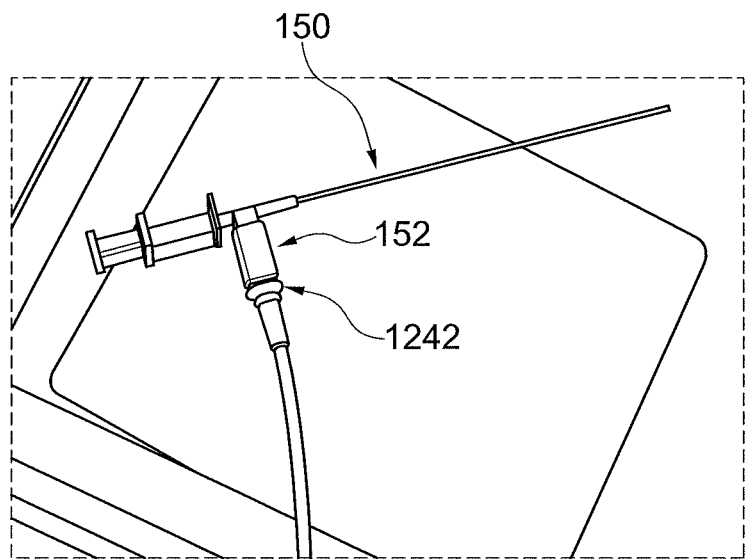
FIG. 2 depicts an instrument to be employed in embodiments of the present invention.

Further still, not only the position/orientation of the physical tissue model 110 may be tracked, but the tracking system 120 may also track the position/orientation of the instrument 150. With reference to FIG. 2 it is noted that the tracking system 120 may also comprise an instrument sensor 1242 (having a configuration identical to the discussed sensor 124) and the instrument 150 may have a section 152 adapted for attachment of the sensor 1242 in a defined orientation. Again, in particular, the section 152 may be adapted to receive the sensor 1242. It will be understood that by means of this configuration, the tracking system 120 may be adapted to track (or sense) the position and orientation of the sensor 1242 and thus also the position and orientation of the instrument 150.

Furthermore, it is noted that the instrument 150 may have a matching instrument model in the data processing means, which may also be referred to as the data instrument model (also referred to as the representation of the instrument 150). Thus, by "knowing" (i.e., sensing) the position and orientation of the instrument 150 in the "real" world, one may also infer the position and orientation of the corresponding or matching data instrument model. Thus, one may also know its position and orientation with respect to the data tissue model, i.e., the data set corresponding to the physical tissue model 120. Thus, one may also display the data instrument model and its position and orientation with respect to the data tissue model on the display device 140. Further still, in some embodiments, the instrument 150 may have different sections that are movable to one another and such movement may also be tracked and displayed by the MS system 100.

In some embodiments, the physical tissue model 110 may comprise different sections, portions or regions of tissue. For example, the solid bone model 118 depicted in FIG. 5 comprises three vertebrae 1182, 1184, 1186, which may also generally be referred to as different tissue sections. In some medical simulations, it may be desirable that such sections (e.g., the vertebrae) are movable with respect to one another. For example, when considering a spinal fusion (where two or more vertebrae are fixed to one another), one may also want to change the location/orientation of the vertebrae, and when simulating such a medical intervention, it may be desirable to also simulate such a movement of the vertebrae. Therefore, the tissue sections 1182, 1184, 1186 (e.g., the vertebrae 1182, 1184, 1186 depicted in FIG. 5) may also be movable with respect to one another. Put differently, the physical tissue model 110 may comprise tissue sections 1182, 1184, 1186 and may be adapted for movement of these tissue sections 1182, 1184, 1186.

Figure 10:
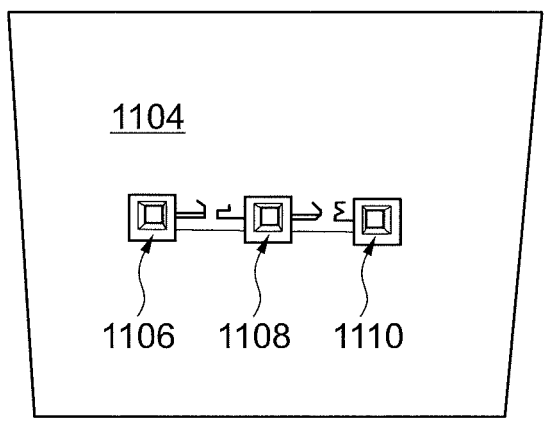
FIG. 10 depicts a further section of a physical tissue model to be employed in embodiments of the present invention.

Furthermore, it may also be desirable that such a relative movement of different model tissue sections 1182, 1184, 1186 can also be tracked or sensed by means the tracking system 120. Then, such movement may also be displayed by the display device 140. In that regard, in the present embodiment, a plurality of tracking sensors 124 may be provided, and more particularly one tracking sensor 124 for each movable tissue section 1182, 1184, 1186, respectively. In that regard, exemplary reference is also made to FIG. 6 depicting a physical tissue model 110 comprising three sensor attachment sections 1106, 1108, 1110, each sensor attachment section 1106, 1108, 1110 being adapted such that a sensor 124 can be attached thereto. Again, in the depicted embodiment, each such sensor attachment section 1106, 1108, 1110 is realized as a recess (which may also be referred to as a cavity) for receiving a respective sensor 124. A further variant of a corresponding embodiment is also depicted in FIG. 10, which Figure depicts a bottom surface 1104 or bottom section 1104 of a physical tissue model (similar to FIG. 9). Also this embodiment comprises three sensor attachment section 1106, 1108, 1110 adapted such that a sensor 124 can be attached to each of these sections 1106, 1108, 1110, wherein, again, these sections 1106, 1108, 1110 are here realized as recesses (put differently: cavities) for receiving the sensors 124.

In the embodiments depicted in FIGS. 6 and 10, there is thus provided one sensor attachment section 1106, 1108, 1110 for each movable model tissue section 1182, 1184,

1186. That is, when one of the movable tissue section 1182, 1184, 1186 moves, the respective sensor associated thereto will also move and this movement can be tracked or sensed by means of the tracking system 120. The respective data tissue model may then be changed according to the sensed movement of the physical tissue model 110 and the respective change may also be displayed on the display device 140. Thus, the MS system 100 also allows the simulation of medical interventions where the relative positions and/or orientations of sections or portions of tissue are altered. Such changes may be tracked and displayed by the MS system 100.

Having different model tissue sections 1182, 1184, 1186 that are movable to one another (and such movement optionally being tracked and displayed) may allow for the realistic simulation of different medical interventions. For example, with such a system, an erection of a fractured (kyphosing) vertebra may be simulated. Furthermore, also corrections of degenerative or congenital kyphoses or kyphoscolioses may be simulated. Such conditions are typically corrected by corrective spondylodesis or osteotomy. By having the different tissue sections (e.g., the vertebrae) 1182, 1184, 1186 movable to one another, such medical interventions (e.g., corrective spondylodesis or osteotomy) may be simulated in a very realistic manner by the discussed MS system 100.

In the above, it has been described that a representation of the data tissue model and the instrument 150 in the data tissue model may be displayed by the displaying device 140. That is, the displaying device 140 may display an image corresponding to the data tissue model and the representation of the instrument 150 in the data tissue model. It will be understood that the exact image being displayed does not only depend on the position and the orientation of the physical tissue model 1110 and the instrument 150, but also on an imaging plane. Generally, in the MS system 100, the imaging plane can be chosen, e.g., by the user. More particularly, the MS system 100 may comprise a control unit 160 for controlling the imaging plane. In the embodiment depicted in FIG. 1, the control unit 160 comprises three control elements for adjusting the imaging plane in degrees of freedom. By means of these control elements, the coordinates of the imaging plane may be adjusted. Further still, the MS system 100 may also comprise an actuation element 170, which may be a foot actuation element 170. When actuating the actuation element 170, a new image may be displayed on the display device 140. This may provide a particularly realistic medical simulation.

For example, when performing a real medical intervention with the help of X-rays (e.g., by using a C-arm), the medical practitioner does not continuously capture images of the tissue and the instrument, as this would lead to an excessive exposure of the patient to the X-rays. Instead, the medical practitioner would only capture images in critical situations, e.g., when reaching a bone, to check the position and/or orientation of the instrument(s) in such critical situations. This can also be simulated with the MS system 100, as the MS system 100 may be adapted to only display a new image of the medical intervention when the actuation element 170 is actuated.

However, the MS system 100 also allows the continuous display of images. To attain this, the actuation element 170 may be continuously actuated. Such a continuous actuation and continuous display of subsequent images may decrease the overall difficulty for a user (as he is continuously supplied with information as regards the position and/or orientation of the instrument 150 with respect to the physical tissue model 110). Such a use of the MS system 100 may be particularly useful for beginners, as it may be easier for a user when being supplied with such continuous information.

A typical use scenario or procedure employing the MS system 100 will now be described. A user, e.g., a healthcare practitioner, such as a medical doctor, may hold the medical instrument 150 in his hand. The medical instrument 150 is brought to the physical tissue model 110 and it may be introduced into the physical tissue model 110, e.g., it may be inserted into the physical tissue model 110 through the elastic layer 114. The user may further push the medical instrument 150 to sink into the gel 116 embedding the solid bone model 118. At a certain point, the medical instrument 150 reaches the physical bone model 118 and the user will feel that, that is, the user will be provided with a haptic feedback once he reaches the physical bone model 118, as the force to further insert the instrument 150 is substantially higher when having to force it into the physical bone model 118 than the force required to force it through the gel 116. In particular, when reaching the physical bone model 118 and pressing the instrument 150 onto the physical bone model 118 (e.g., to force the instrument into the physical bone model 118), the physical tissue model 110 may yield due to the resilient or flexible support 1102. This may provide a particularly realistic feedback to the user.

At any time of the described procedure, the position and orientation of the instrument 150 is monitored by means of the described tracking system 120. Furthermore, also the position and orientation of the physical tissue model 110 is monitored by the tracking system 120. As described, the physical tissue model 110 has a corresponding or matching data tissue model in the data processing means 130. As also described, the instrument 150 has a corresponding virtual or data instrument in the data processing means 130. The position and orientations of the data tissue model and the data instrument are changed in accordance with the positions and orientations that are sensed for the physical tissue model 110 and the instrument 150. A corresponding image may also be displayed on the display device 140, either continuously or when the actuation element 170 is actuated. More particularly, the user may select the imaging plane by means of the control element 160 and may actuate the actuation element 170 to display a corresponding image on the display device 140.

As also discussed, the physical tissue model 110 may comprise different tissue sections 1182, 1184, 1186 that may be movable with respect to one another and such movements may also be tracked by the MS system 100. Furthermore, the data tissue model in the data processing means 130 may comprise corresponding data tissue sections (e.g., 3 vertebra sections, each such vertebra section corresponding to a vertebra section 1182, 1184, 1186 of the physical tissue model 110). Again, when a movement of the physical tissue sections 1182, 1184, 1186 is sensed, the corresponding data tissue sections may also be rearranged accordingly and, e.g., when the user actuates the actuation element 170, a corresponding image may be displayed on the display device 140.

Furthermore, it should be noted that the data tissue model in the data processing means 130 may also be altered in response to the tracked position and/or orientation of the instrument 150. If, for example, the instrument 150 is a drill, the data tissue model would typically change once it is contacted by the instrument 150. Furthermore (though not depicted), the described embodiments may also be used for simulation of a medical intervention using an implant.

In the above, particular embodiments of the present invention have been described. However, it should be understood that the described embodiments are merely exemplary and should not limit the scope of the present invention. To the contrary, modifications are possible without departing from the scope of the present invention. For example, while in the above, the tracking system 120 has been described to be an electromagnetic tracking system 120, other tracking systems 120 may be employed. Such other tracking systems 120 may employ depth sensors (such as 3D-cameras, stereo cameras, TOF cameras, Lightfields, or marker-based sensors), optical tracking and/or ultrasound tracking. Furthermore, the present technology may also employ mechanical tracking systems, e.g., tracking systems that track the position and/or orientation of an object by means of one or more movable mechanical arms.

Furthermore, in the above, the present invention has been described with reference to a physical tissue model 110 representing, inter alia, bone tissue. However, the present invention may also be employed to simulate a medical intervention in soft tissue. If the relative movement of such a soft tissue was to be tracked, one would have to employ a "continuous tracking", rather than a "discrete tracking", as is the case when the only the relative positions/orientations of discrete blocks of tissue (such as three vertebrae 1182, 1184, 1186) is to be tracked. Such a continuous tracking may be realized in different manners, for example, by means of optical tracking. However, the described electromagnetic tracking may also be used in such a scenario with different sensors located in the soft tissue model (such as, one sensor per 1 $(cm)^2$ or per 8 $(cm)^2$) and an interpolation for positions between such sensors. Furthermore, a Bragg Fiber Grating could also be used in such a scenario to track the position and orientation of the different regions of the tissue model. Such a Bragg Fiber Grating would typically comprises one or more Bragg Fiber Grating sensors.

Further still, it should be noted that the present technology may be used to simulate medical interventions performed with different medical imaging techniques. Such simulated medical imaging techniques may include CBCT, CT, MRI, US, PET, SPECT, OCT, and/or gamma probe. Each such imaging technique may be simulated by the present technology. In particular, the present technology may be employed without actually performing the real imaging, but by just simulating it as discussed above. This may be advantageous as it does not expose the user to any radiation. Generally, dummy imaging devices (which may also be referred to as dummy imaging devices) may be used and their positions and/or orientation may be tracked by the tracking system to determine the imaging plane. As a mere example, a dummy US probe may be used and depending on its orientation and/or position (which may be tracked) the imaging plane and hence the image displayed on the display device may be determined.

Whenever a relative term, such as "about", "substantially" or "approximately" is used in this specification, such a term should also be construed to also include the exact term. That is, e.g., "substantially straight" should be construed to also include "(exactly) straight".

Whenever steps were recited in the above or also in the appended claims, it should be noted that the order in which the steps are recited in this text may be accidental. That is, unless otherwise specified or unless clear to the skilled person, the order in which steps are recited may be accidental. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), followed by step (Z). Corresponding considerations apply when terms like "after" or "before" are used.

While in the above, a preferred embodiment has been described with reference to the accompanying drawings, the skilled person will understand that this embodiment was provided for illustrative purpose only and should by no means be construed to limit the scope of the present invention, which is defined by the claims.

The invention claimed is:

1. A medical simulation system, comprising:
a physical tissue model;
an instrument; and
a tracking system adapted to track at least a position and/or an orientation of the physical tissue model and a position and/or an orientation of the instrument,
wherein the physical tissue model comprises a tissue model portion and a support structure supporting the tissue model portion and wherein the support structure is elastic;
wherein the tissue model portion comprises a plurality of portions that are movable with respect to one another; and
wherein the tracking system is configured to track a position and an orientation of each of the plurality of the portions;
wherein the physical tissue model further comprises a gel and/or foam at least partially embedding the tissue model portion; and
wherein the tissue model portion is adapted to move in response to a force supplied by the instrument.

2. The medical simulation system according to claim 1, wherein the instrument comprises a plurality of instrument sections that are movable with respect to one another and wherein the tracking system is configured to track a position and an orientation of each of the plurality of the instrument sections.

3. The medical simulation system according to claim 1, further comprising a data processing means.

4. The medical simulation system according to claim 3, wherein the medical simulation system further comprises a display device adapted to display an image based on information on the data processing means, wherein the medical simulation system comprises an actuation element and wherein the medical simulation system is configured to update the image when the actuation element is actuated.

5. The medical simulation system according to claim 1, further comprising a data processing means, wherein a tissue model data set is stored in the data processing means, the tissue model data set corresponding to the physical tissue model, and wherein the data processing means is configured to alter the tissue model data set based on the tracked positions and/or orientations of the plurality of portions that are movable with respect to one another.

6. The medical simulation system according to claim 5, wherein the data processing means is configured to alter the tissue model data set based on the tracked position and/or orientation of the instrument and the physical tissue model.

7. The medical simulation system according to claim 1, further comprising a data processing means, wherein:
the instrument comprises a plurality of instrument sections that are movable with respect to one another and wherein the tracking system is configured to track a position and an orientation of each of the plurality of the instrument sections; and a representation of the instrument is stored in the data processing means, and the data processing means is configured to alter the representation of the instrument based on the tracked positions and/or orientations of the instrument sections.

8. The medical simulation system according to claim 1, wherein the medical simulation system is configured to simulate a medical imaging technique and wherein the medical simulation system does not comprise a real medical imaging device adapted to perform the medical imaging technique.

9. Use of the medical simulation system according to claim 1 for simulating a medical intervention.

10. A method of simulating a medical intervention, wherein the method uses a medical simulation system comprising:

a physical tissue model, an instrument, and a tracking system adapted to track at least a position and/or an orientation of the physical tissue model and a position and/or an orientation of the instrument, wherein the physical tissue model comprises a tissue model portion and a support structure supporting the tissue model portion, wherein the support structure is elastic wherein the tissue model portion comprises a plurality of portions that are movable with respect to one another, wherein the tracking system is configured to track a position and an orientation of each of the plurality of the portions, wherein the physical tissue model further comprises a gel and/or foam at least partially embedding the tissue model portion; and wherein the tissue model portion is adapted to move in response to a force supplied by the instrument, the method comprising:

contacting, using the instrument, the physical tissue model;

tracking, using the tracking system, a position and/or an orientation of the instrument;

tracking, using the tracking system, a position and/or an orientation of the physical tissue model;

compressing, due to a force being supplied to the physical tissue model, the support structure; and tracking, using the tracking system, the position and the orientation of the plurality of portions.

11. The method according to claim 10, wherein the medical simulation system further comprises data processing means, wherein a tissue model data set is stored in the data processing means, the tissue model data set corresponding to the physical tissue model, wherein the method further comprises:

altering, using the data processing means, the tissue model data set based on the tracked positions and/or orientations of the plurality of portions that are movable with respect to one another.

12. The method according to claim 11, further comprising:

altering, using the data processing means, the tissue model data set based on the tracked position and/or orientation of the instrument and the physical tissue model.

* * * * *